(12) United States Patent
Trieu

(10) Patent No.: US 7,771,414 B2
(45) Date of Patent: Aug. 10, 2010

(54) CONTROLLED RELEASE DEVICES FOR THERAPEUTIC TREATMENTS OF SPINAL DISCS

(75) Inventor: Hai H. Trieu, Cordova, TN (US)

(73) Assignee: Warsaw Orthopedic, Inc.

( * ) Notice: Subject to any disclaimer, the term of this patent is extended or adjusted under 35 U.S.C. 154(b) by 1117 days.

(21) Appl. No.: 11/410,221

(22) Filed: Apr. 24, 2006

(65) Prior Publication Data

US 2007/0250046 A1 Oct. 25, 2007

(51) Int. Cl.
*A61K 9/22* (2006.01)
(52) U.S. Cl. ............... 604/892.1; 604/891.1; 604/65; 604/66; 623/17.12
(58) Field of Classification Search .......... 604/891.1, 604/892.1, 65, 66, 67; 623/17.11, 17.12, 623/17.13, 17.15, 17.16
See application file for complete search history.

(56) References Cited

U.S. PATENT DOCUMENTS

| | | | |
|---|---|---|---|
| 3,320,131 A | 5/1967 | Smith | |
| 3,941,127 A | 3/1976 | Froning | |
| 3,964,480 A | 6/1976 | Froning | |
| 4,039,682 A | 8/1977 | Ausman et al. | |
| 4,374,926 A | 2/1983 | Stern | |
| 4,430,760 A | 2/1984 | Smestad | |
| 4,439,423 A | 3/1984 | Smith | |
| 4,696,816 A | 9/1987 | Brown | |
| 4,719,108 A | 1/1988 | Smith | |
| 4,904,260 A | 2/1990 | Ray et al. | |
| 5,422,103 A | 6/1995 | Stern et al. | |
| 5,456,679 A * | 10/1995 | Balaban et al. | 604/892.1 |
| 5,468,480 A | 11/1995 | Barrett et al. | |
| 5,645,549 A | 7/1997 | Boyd et al. | |
| 5,919,235 A | 7/1999 | Husson et al. | |
| 6,007,810 A | 12/1999 | Ishikawa et al. | |
| 6,063,378 A | 5/2000 | Nohara et al. | |
| 6,231,615 B1 | 5/2001 | Preissman | |
| 6,280,475 B1 | 8/2001 | Bao et al. | |
| 6,294,187 B1 | 9/2001 | Boyce et al. | |
| 6,471,688 B1 * | 10/2002 | Harper et al. | 604/892.1 |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |

(Continued)

FOREIGN PATENT DOCUMENTS

WO  WO 96/34093  10/1996

(Continued)

OTHER PUBLICATIONS

NCBI; "Fibroblast Growth Factor [*Homo sapiens*]"; CAA41788; http:www.nebi.nlm.nih.gov/protein/1335059; printed on May 14, 2009; 2 pages.

(Continued)

*Primary Examiner*—Kevin C Sirmons
*Assistant Examiner*—Bhisma Mehta

(57) ABSTRACT

A device includes a first reservoir configured to include a degrading agent, a first valve in fluid communication with the first reservoir, and a reservoir driver configured to manipulate the first reservoir to effect a first reservoir condition based on a first tissue condition. The first valve is configured to open in response to the first reservoir condition associated with the first reservoir.

13 Claims, 11 Drawing Sheets

U.S. PATENT DOCUMENTS

| | | | |
|---|---|---|---|
| 6,551,838 B2 | 4/2003 | Santini, Jr. et al. |
| 6,656,162 B2 | 12/2003 | Santini, Jr. et al. |
| 6,669,683 B2 | 12/2003 | Santini, Jr. et al. |
| 6,773,429 B2 | 8/2004 | Sheppard, Jr. et al. |
| 6,827,250 B2 | 12/2004 | Uhland et al. |
| 6,849,463 B2 | 2/2005 | Santini, Jr. et al. |
| 6,973,718 B2 | 12/2005 | Sheppard, Jr. et al. |
| 6,976,982 B2 | 12/2005 | Santini, Jr. et al. |
| 7,014,636 B2 | 3/2006 | Gilbert |
| 7,163,545 B2 | 1/2007 | Yaszemski et al. |
| 7,169,405 B2 | 1/2007 | Trieu |
| 7,217,293 B2 | 5/2007 | Branch, Jr. |
| 2001/0020188 A1 | 9/2001 | Sander |
| 2002/0026244 A1 | 2/2002 | Trieu |
| 2002/0029083 A1 | 3/2002 | Zucherman et al. |
| 2002/0087113 A1 | 7/2002 | Hartlaub |
| 2002/0128202 A1 | 9/2002 | Carney et al. |
| 2002/0173851 A1 | 11/2002 | McKay |
| 2003/0009235 A1 | 1/2003 | Manrique et al. |
| 2003/0039676 A1 | 2/2003 | Boyce et al. |
| 2004/0031666 A1 | 2/2004 | Ostman |
| 2004/0091540 A1 | 5/2004 | Desrosiers et al. |
| 2004/0121486 A1 | 6/2004 | Uhland et al. |
| 2004/0133280 A1 | 7/2004 | Trieu |
| 2004/0143242 A1* | 7/2004 | Ludin et al. ............... 604/891.1 |
| 2004/0220552 A1 | 11/2004 | Heruth et al. |
| 2005/0031666 A1 | 2/2005 | Trieu |
| 2005/0070778 A1 | 3/2005 | Lackey et al. |
| 2005/0071009 A1 | 3/2005 | Muhanna et al. |
| 2006/0004456 A1 | 1/2006 | McKay |
| 2006/0046961 A1 | 3/2006 | McKay et al. |
| 2006/0047341 A1 | 3/2006 | Trieu |
| 2007/0003598 A1 | 1/2007 | Trieu |
| 2007/0250044 A1* | 10/2007 | Trieu ....................... 604/890.1 |
| 2007/0250045 A1 | 10/2007 | Trieu |
| 2007/0276337 A1 | 11/2007 | Trieu |

FOREIGN PATENT DOCUMENTS

| | | | |
|---|---|---|---|
| WO | 0145577 A2 | 6/2001 |
| WO | 01045577 A3 | 6/2001 |
| WO | 0217824 A2 | 3/2002 |
| WO | 0217824 A3 | 3/2002 |
| WO | 03068149 A2 | 8/2003 |
| WO | 03068149 A3 | 8/2003 |
| WO | 2004047691 A | 6/2004 |
| WO | WO 2004/101015 A2 | 11/2004 |
| WO | 2005065079 A2 | 7/2005 |
| WO | 2005092249 A1 | 10/2005 |
| WO | WO 2005/102440 A2 | 11/2005 |
| WO | WO 2005/115438 A1 | 12/2005 |
| WO | WO 2006/017456 A2 | 2/2006 |
| WO | 2006050106 A | 5/2006 |
| WO | 2006055547 A | 5/2006 |
| WO | 2007127548 A | 11/2007 |

OTHER PUBLICATIONS

NCBI; "[*Homo sapiens*]"; CAA00606; http:www.nebi.nlm.nih.gov/protein/412163; printed on May 14, 2009; 2 pages.

NCBI; "Chymopapain [*Carica papaya*]"; CAA66378; http:www.nebi.nlm.nih.gov/protein/1332461; printed on May 14, 2009; 2 pages.

NCBI ; "Collagenas [*Rattus novegicus*]"; CAA07432; http:www.nebi.nlm.nih.gov/protein/3242321; printed on May 14, 2009; 3 pages.

NCBI; "Morphogenetic Protein [*Bacillus subtilis* Subsp. Subtilis Str. 168]"; NP_391488; http:www.nebi.nlm.nih.gov/protein/16080660; printed on May 14, 2009; 3 pages.

Sheikh H et al. 2009. In vivo intervertebral disc regeneration using stem cell-derived chondropogenitors. J Neurosurg Spine 10: 265-272.

Bron JL et al. 2009. Repair, regenerative and supportive therapies of the annulus fibrosus: achievements and challenges. Eur Spine J 18:301-313.

Chymopapain from GenBank Accession No. CAA66378, pp. 1-2. Accessed May 14, 2009.

Collagenase from GenBank Accession No. CAA07432, pp. 1-3. Accessed May 14, 2009.

Fibroblast growth factor from GenBank Accession No. CAA41788, pp. 1-2. Accessed May 14, 2009.

Morphogenetic protein from GenBank Accession No. NP_391488, pp. 1-3. Accessed May 14, 2009.

Albumin from GenBank Accession No. CAA00606, pp. 1-2. Accessed May 14, 2009.

\* cited by examiner

CONTROLLED RELEASE DEVICES FOR THERAPEUTIC TREATMENTS OF SPINAL DISCS

FIELD OF THE DISCLOSURE

The present disclosure relates generally to controlled release devices. More specifically, the present disclosure relates to controlled release devices for implanting in an intervertebral disc.

BACKGROUND

In human anatomy, the spine is a generally flexible column that can take tensile and compressive loads. The spine also allows bending motion and provides a place of attachment for keels, muscles, and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column can be subjected. At the same time, the intervertebral discs can allow adjacent vertebral bodies to move relative to each other, particularly during bending or flexure of the spine. Thus, the intervertebral discs are under constant muscular and gravitational pressure and generally, the intervertebral discs are the first parts of the lumbar spine to show signs of deterioration.

In particular, deterioration can be manifested as a herniated disc. Weakness in an annulus fibrosis can result in a bulging of the nucleus pulposus or a herniation of the nucleus pulposus through the annulus fibrosis. Ultimately, weakness of the annulus fibrosis can result in a tear permitting the nucleus pulposus to leak from the intervertebral space. Loss of the nucleus pulposus or a bulging of the nucleus pulposus can lead to pinching of nerves and contact between osteal surfaces, causing pain and damage to vertebrae. In addition, aging can lead to a reduction in the hydration of the nucleus pulposus. Such a loss in hydration can also permit contact between osteal surfaces and pinching of nerves.

While replacement of the disc in the intervertebral space with an implant is an option, many surgeons seek a less invasive procedure. One such procedure for alleviating a bulging disc is injection of chemonucleolytic agents to dissolve a portion of the nucleus pulposus, drawing the herniated or bulging portion of the nucleus pulposus back to the center of the intervertebral disc. However, such injections can leak into sensitive regions outside of the intervertebral disc, leading to medical complications. Other attempts to alleviate bulging discs include implanting slowly dissolving solid matrices that include a chemonucleolytic agent. Once implanted, the solid matrices slowly dissolve, substantially releasing the chemonucleolytic agent, sometimes resulting in degradation of an excess amount of the nucleus pulposus.

DESCRIPTION OF DRAWINGS

Figure 1:
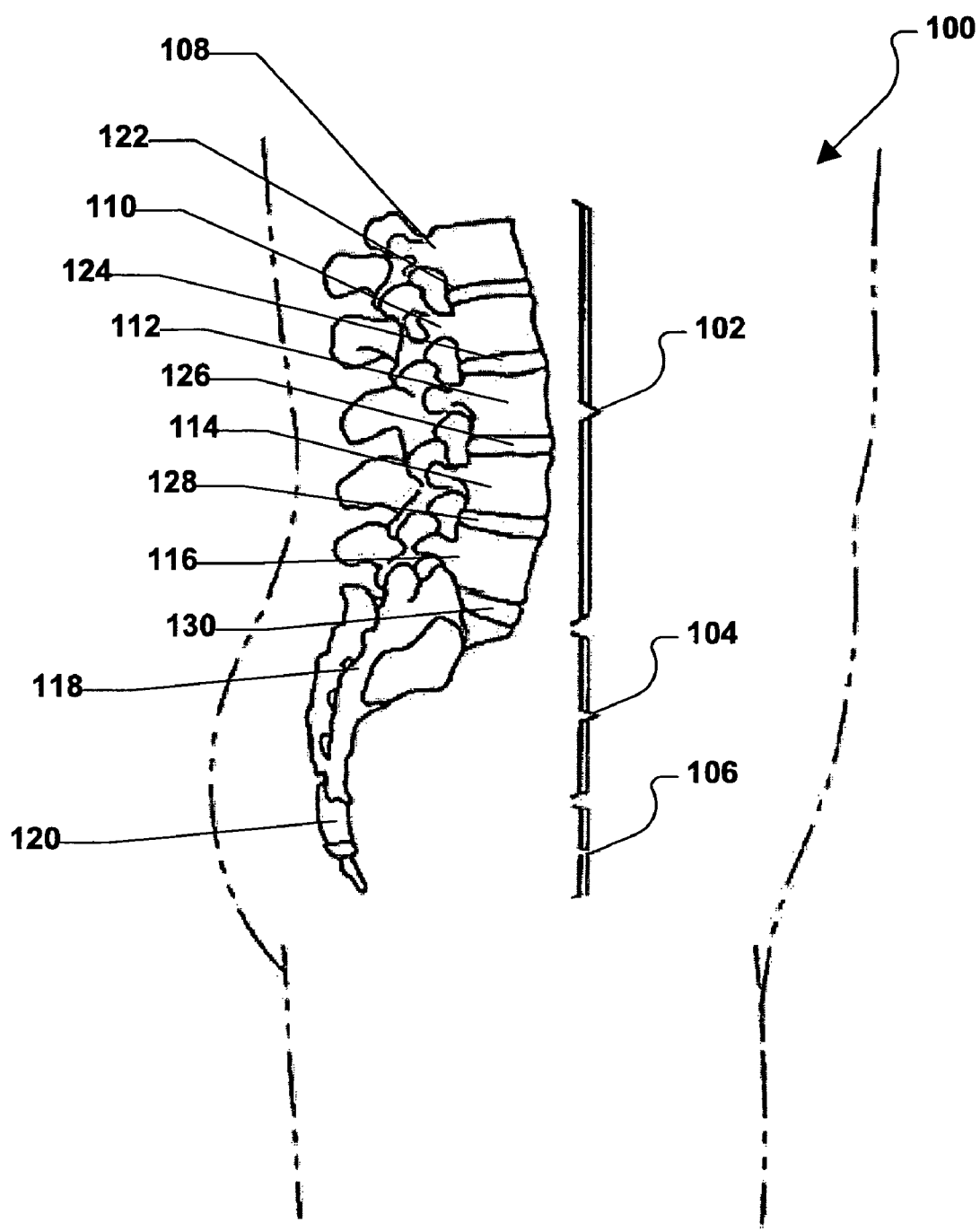
FIG. 1 includes a lateral view of a portion of a vertebral column.

In a particular embodiment, a controlled release device includes a reservoir driver connected to a reservoir. The reservoir driver influences the condition of the reservoir and a valve connected to the reservoir based on a condition of a tissue in which the device can be implanted. In an example, the reservoir includes an agent, such as a stimulating agent or a degrading agent. In addition, the device can include a second reservoir.

In an exemplary embodiment, a device includes a first reservoir configured to include a degrading agent, a first valve in fluid communication with the first reservoir, and a reservoir driver configured to manipulate the first reservoir to effect a first reservoir condition based on a first tissue condition. The first valve is configured to open in response to the first reservoir condition associated with the first reservoir.

In another exemplary embodiment, a device includes a first reservoir, a second reservoir, a first valve in fluid communication with the first reservoir, and a second valve in fluid communication with the second reservoir. The first valve is configured to open based on a first tissue condition. The second valve is configured to open based on a second tissue condition.

In a further exemplary embodiment, a device includes a first reservoir configured to include a stimulating agent, a second reservoir configured to include a degrading agent, a first valve in fluid communication with the first reservoir, and a second valve in fluid communication with the second reservoir. The first valve is configured to close in response to a high-pressure condition in the first reservoir and the second valve is configured to open in response to a high-pressure condition in the second reservoir.

In an additional exemplary embodiment, a device includes a first reservoir configured to include a stimulating agent, a second reservoir configured to include a degrading agent, a first valve in fluid communication with the first reservoir, a second valve in fluid communication with the second reservoir, and an osmotic reservoir driver configured to apply pressure to at least one of the first or second reservoirs based on a condition of a tissue. The first valve is configured to open in response to a low-pressure condition in the first reservoir, and the second valve is configured to open in response to a high-pressure condition in the second reservoir.

In a further exemplary embodiment, a device includes a first reservoir configured to include a stimulating agent, a second reservoir configured to include a degrading agent, and a three-way valve configured to provide fluid communication with the first reservoir in response to a first tissue condition and configured to provide fluid communication with the second reservoir in response to a second tissue condition.

In another exemplary embodiment, a method of preparing a controlled release device includes selecting a controlled release agent configured to affect a condition of a nucleus pulposus and selecting a valve configuration.

Description of Relevant Anatomy

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged that intervertebral lumbar disc 122, 124, 126, 128, 130 can be at least partially treated with an intervertebral implanted device according to one or more of the embodiments described herein. In a particular embodiment, a controlled release device can be inserted into the intervertebral lumbar disc 122, 124, 126, 128, 130.

Figure 2:
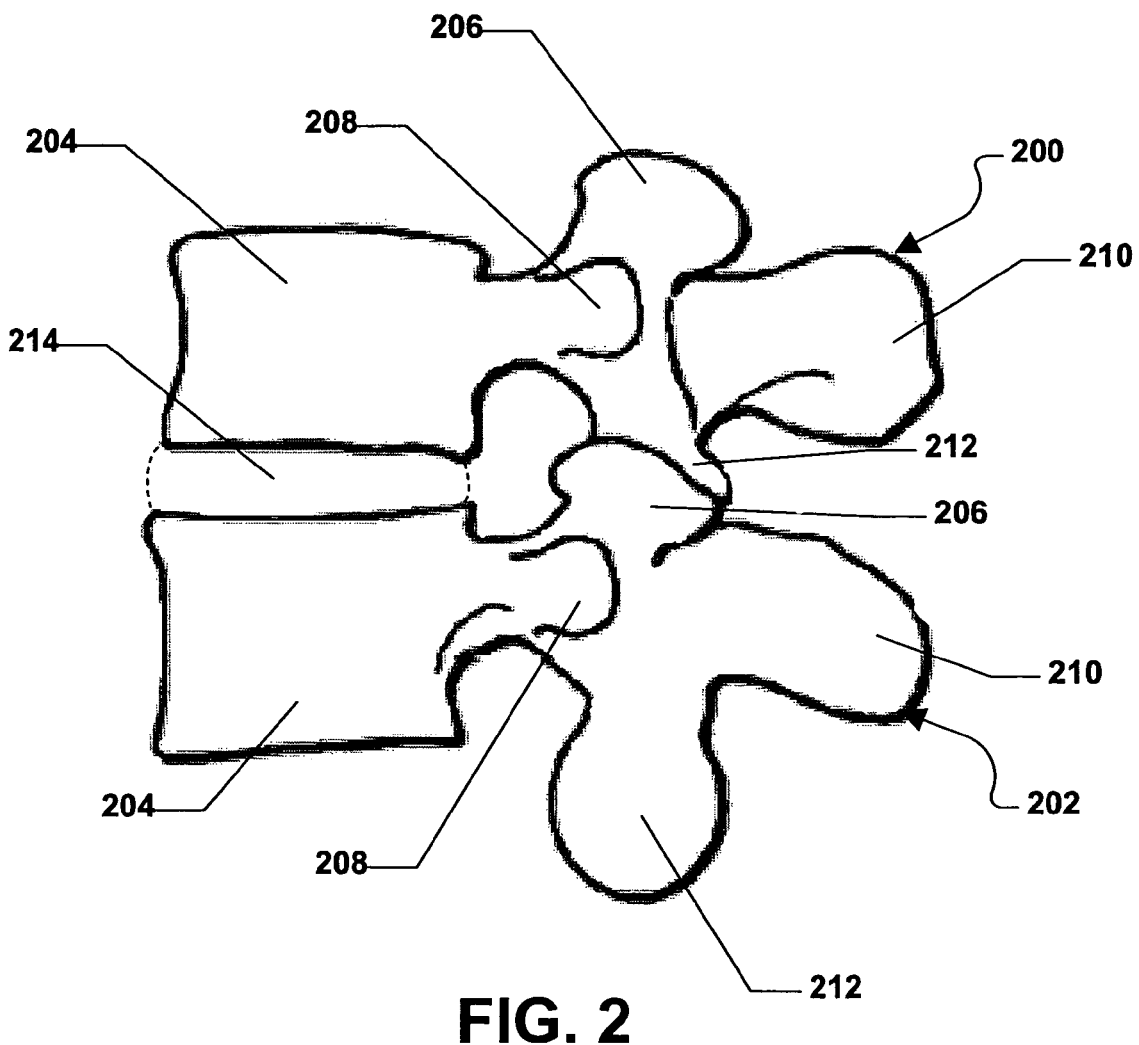
FIG. 2 includes a lateral view of a pair of adjacent vertebrae.

FIG. 2 depicts a detailed lateral view of two adjacent vertebrae, e.g., two of the lumbar vertebra 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 214 between the superior vertebra 200 and the inferior vertebra 202. As described in greater detail below, an intervertebral controlled release device according to one or more of the embodiments described herein can be installed within the intervertebral disc 214 between the superior vertebra 200 and the inferior vertebra 202.

Figure 3:
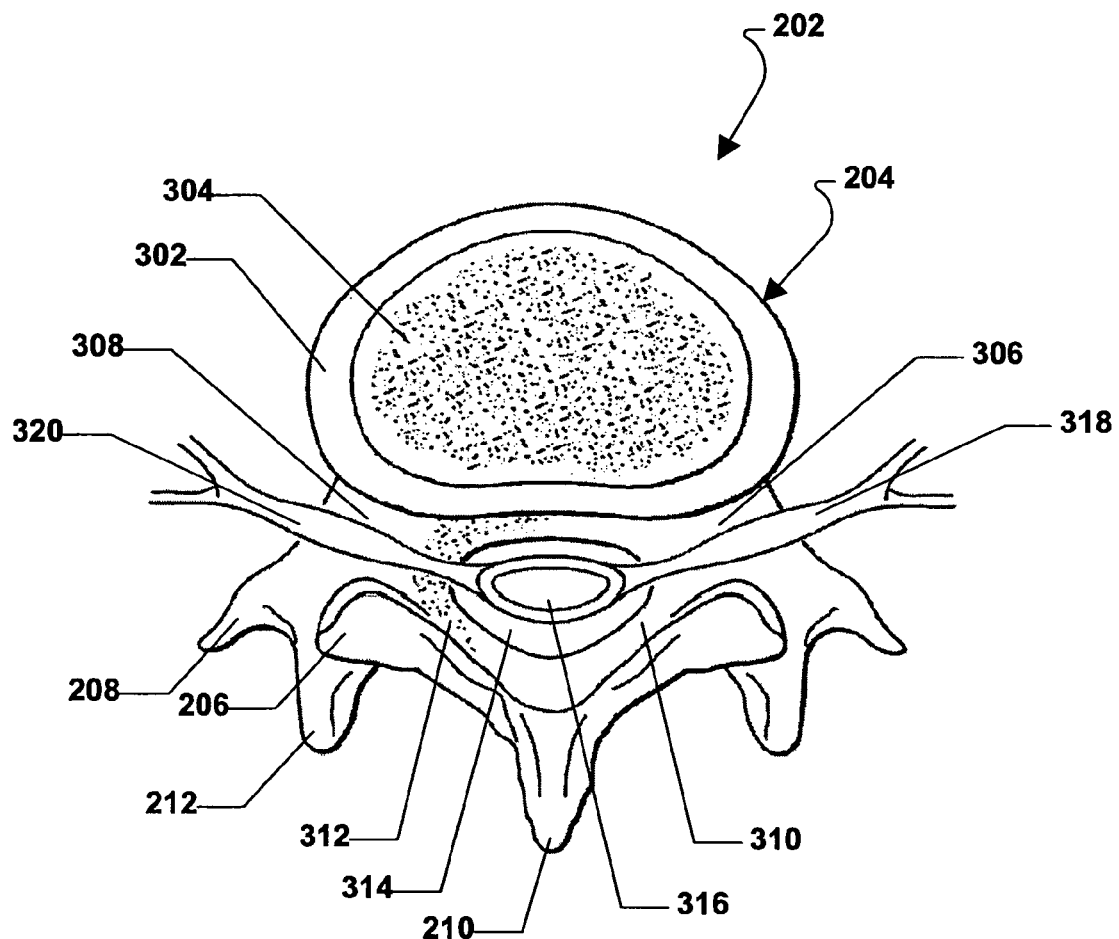
FIG. 3 includes a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
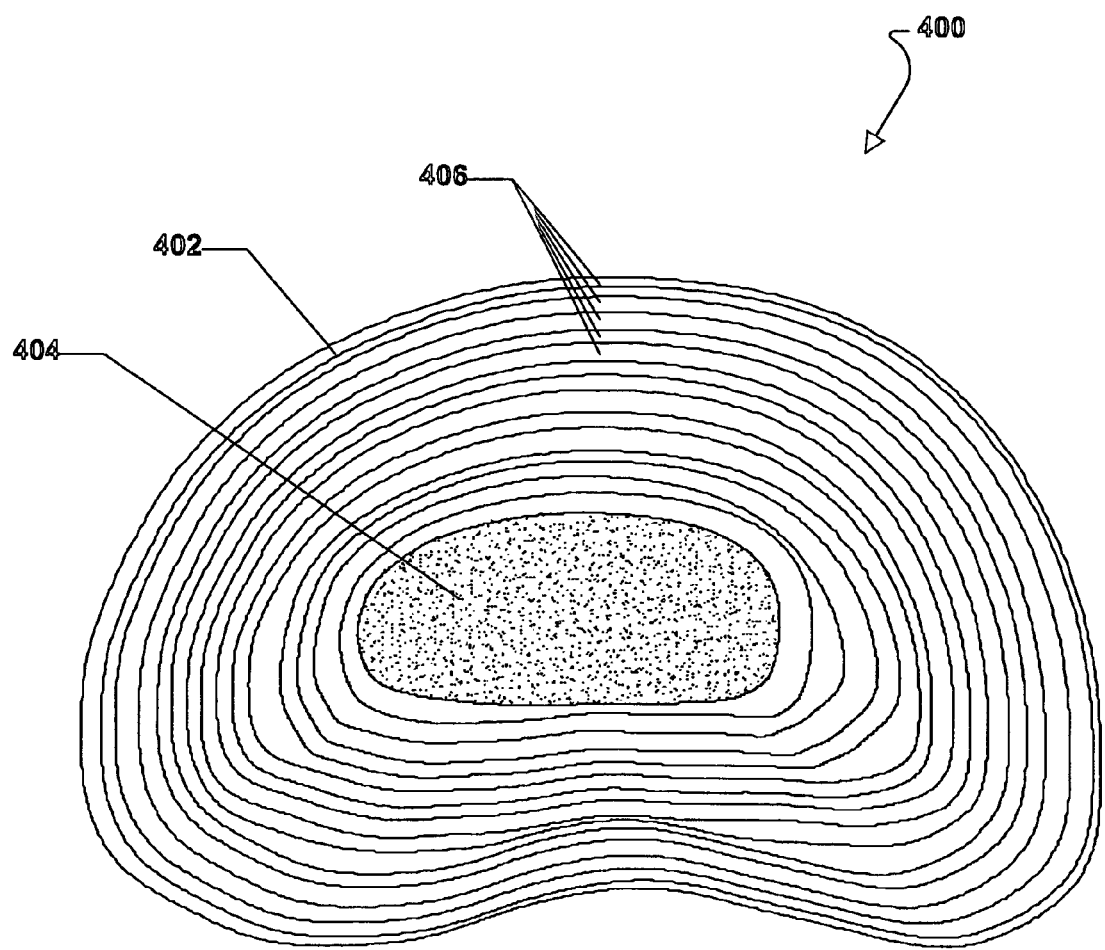
FIG. 4 includes a cross section view of an intervertebral disc.

Referring now to FIG. 4, an intervertebral disc is shown and is generally designated 400. The intervertebral disc 400 is made up of two components: the annulus fibrosis 402 and the nucleus pulposus 404. The annulus fibrosis 402 is the outer portion of the intervertebral disc 400, and the annulus fibrosis 402 includes a plurality of lamellae 406. The lamellae 406 are layers of collagen and proteins. Each lamella 406 includes fibers that slant at 30-degree angles, and the fibers of each lamella 406 run in a direction opposite the adjacent layers. Accordingly, the annulus fibrosis 402 is a structure that is exceptionally strong, yet extremely flexible.

The nucleus pulposus 404 is the inner gel material that is surrounded by the annulus fibrosis 402. It makes up about forty percent (40%) of the intervertebral disc 400 by weight. Moreover, the nucleus pulposus 404 can be considered a ball-like gel that is contained within the lamellae 406. The nucleus pulposus 404 includes loose collagen fibers, water, and proteins. The water content of the nucleus pulposus 404 is about ninety percent (90%) by weight at birth and decreases to about seventy percent by weight (70%) by the fifth decade.

Injury or aging of the annulus fibrosis 402 can allow the nucleus pulposus 404 to be squeezed through the annulus fibers either partially, causing the disc to bulge, or completely, allowing the disc material to escape the intervertebral disc 400. The bulging disc or nucleus material can compress the nerves or spinal cord, causing pain. Accordingly, the nucleus pulposus 404 can be treated with an implantable controlled release device to improve the condition of the intervertebral disc 400.

Description of Agents

In an exemplary embodiment, a device to be implanted at least partially in the nucleus pulposus of an intervertebral disc includes at least one reservoir to store an agent. The agent can generally affect a condition of the nucleus pulposus. For example, the agent can decrease the hydration level of the nucleus pulposus or can cause a degeneration of the nucleus pulposus that leads to a reduction in hydration level, to a reduction in pressure, or to a reduction in size of the nucleus pulposus within the intervertebral disc. An agent causing a degeneration of the disc or reduction in hydration level is herein termed a "degrading agent." In another example, an agent can increase the hydration level of the nucleus pulposus or can cause a regeneration of the nucleus pulposus that results in an increase in hydration level or in an increase in pressure within the intervertebral disc. Such an agent that causes an increase in hydration or that causes a regeneration of the nucleus pulposus is herein termed a "regenerating agent." In a further example, an agent (herein termed a "therapeutic agent") can inhibit degradation of the nucleus pulposus or enhance maintenance of the nucleus pulposus. Herein, a therapeutic agent or a regenerating agent is collectively referred to as a "stimulating agent."

An exemplary degrading agent can reduce hydration levels in the nucleus pulposus or can degrade the nucleus pulposus, resulting in a reduction in hydration level or in pressure within the intervertebral disc. For example, the degrading agent can be a nucleolytic agent that acts on portions of the nucleus pulposus. In an example, the nucleolytic agent is proteolytic, which breaks down proteins.

An exemplary nucleolytic agent includes a chemonucleolysis agent, such as chymopapain, collagenase, chondroitinase, keratanase, human proteolytic enzymes, papaya protenase, or any combination thereof. An exemplary chondroitinase can include chondroitinase ABC, chondroitinase AC, chondroitinase ACII, chondroitinase ACIII, chondroitinase B, chondroitinase C, or the like, or any combination thereof. In another example, a keratanase can include endo-β-galactosidase derived from *Escherichia freundii*, endo-β-galactosidase derived from *Pseudomonas* sp. IFO-13309 strain, endo-β-galactosidase produced by *Pseudomonas reptilivora*, endo-β-N-acetylglucosaminidase derived from *Bacillus* sp. Ks36, endo-β-N-acetylglucosaminidase derived from *Bacillus circulans* KsT202, or the like, or any combination thereof. In a particular example, the degrading agent includes chymopapain. In another example, the degrading agent includes chondroitinase-ABC.

An exemplary regenerating agent includes a growth factor. The growth factor can be generally suited to promote the formation of tissues, especially of the type(s) naturally occurring as components of an intervertebral disc. For example, the growth factor can promote the growth or viability of tissue or cell types occurring in the nucleus pulposus, such as nucleus pulposus cells or chondrocytes, as well as space filling cells, such as fibroblasts, or connective tissue cells, such as ligament or tendon cells. Alternatively or in addition, the growth factor can promote the growth or viability of tissue types occurring in the annulus fibrosis, as well as space filling cells, such as fibroblasts, or connective tissue cells, such as ligament or tendon cells. An exemplary growth factor can include transforming growth factor-β (TGF-β) or a member of the TGF-β superfamily, fibroblast growth factor (FGF) or a member of the FGF family, platelet derived growth factor (PDGF) or a member of the PDGF family, a member of the hedgehog family of proteins, interleukin, insulin-like growth factor (IGF) or a member of the IGF family, colony stimulating factor (CSF) or a member of the CSF family, growth differentiation factor (GDF), cartilage derived growth factor (CDGF), cartilage derived morphogenic proteins (CDMP), bone morphogenetic protein (BMP), or any combination thereof. In particular, an exemplary growth factor includes transforming growth factor P protein, bone morphogenetic protein, fibroblast growth factor, platelet-derived growth factor, insulin-like growth factor, or any combination thereof.

An exemplary therapeutic agent can include a soluble tumor necrosis factor α-receptor, a pegylated soluble tumor necrosis factor α-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, an inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof. Another exemplary therapeutic agent can include Adalimumab, Infliximab, Etanercept, Pegsunercept (PEG sTNF-R1), Onercept, Kineret®, sTNF-R1, CDP-870, CDP-571, CNI-1493, RDP58, ISIS 104838, 1→3-β-D-glucan, Lenercept, PEG-sTNFRII Fc Mutein, D2E7, Afelimomab, AMG 108, 6-methoxy-2-napthylacetic acid or betamethasone, capsaiein, civanide, TNFRc, ISIS2302 and GI 129471, integrin antagonist, alpha-4 beta-7 integrin antagonist, cell adhesion inhibitor, interferon gamma antagonist, CTLA4-Ig agonist/antagonist (BMS-188667), CD40 ligand antagonist, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-10, HuMax IL-15 (anti-IL 15 antibody), or any combination thereof.

In addition, pain medication can be incorporated within the reservoir in which the agent is contained or in a separate reservoir. An exemplary pain medication includes codeine, propoxyphene, hydrocodone, oxycodone, or any combination thereof.

Each of the agents can be maintained in liquid, gel, paste, slurry, or solid form, or any combination thereof. Solid forms include powder, granules, microspheres, miniature rods, or embedded in a matrix or binder material, or any combination thereof. In an example, fluids or water from surrounding tissues can be absorbed by the device and placed in contact with a drug in solid form prior to release. Further, a stabilizer or a preservative can be included with the agent to prolong activity of the agent.

Description of a Device

In a particular embodiment, an implantable device includes at least one reservoir configured to include an agent. In addition, the implantable device includes at least one valve connected to the reservoir and at least one reservoir driver connected to the at least one reservoir.

Figure 5:
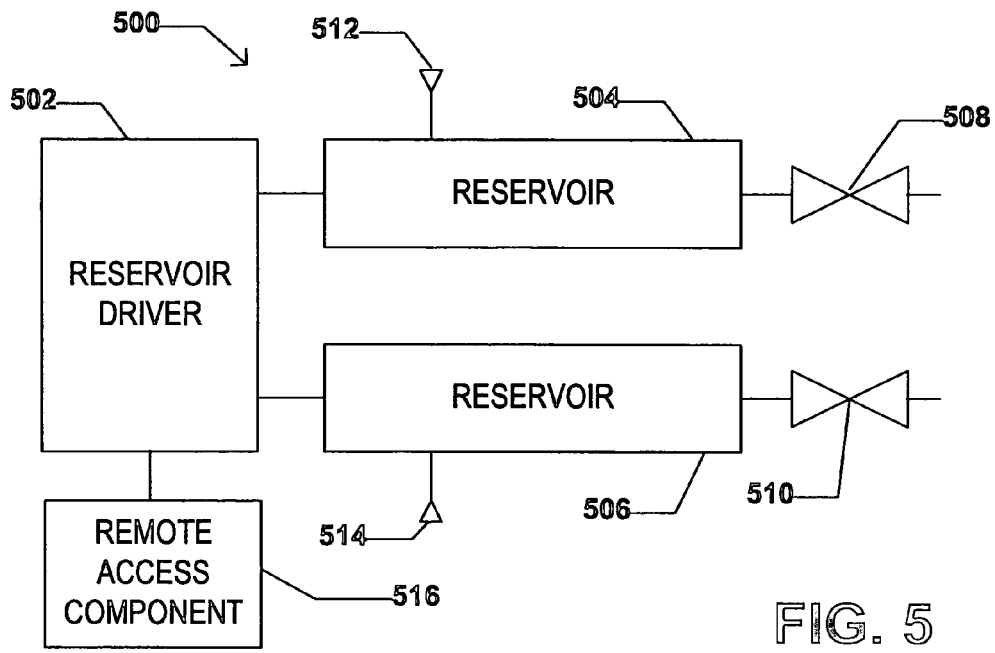
FIG. 5 includes an illustration of an exemplary controlled release device.

FIG. 5 illustrates an exemplary controlled release device 500 to be implanted in a nucleus pulposus of an intervertebral disc. For example, the device 500 can include a reservoir driver 502 connected to a reservoir 504. The reservoir 504 can be configured to include an agent configured to influence a condition of a surrounding tissue, such as a nucleus pulposus. In an example, the reservoir 504 includes a degrading agent. The reservoir 504 can be connected to a valve 508. For example, the valve 508 can be in fluid communication with the reservoir 504. In an example, the valve 508 can open or close in response to pressure within the reservoir 504.

In addition, the device 500 can include a reservoir 506. The reservoir 506 can include a second agent, such as a stimulating agent or a degrading agent. In another example, the second agent can be a pain medication. The reservoir 506 can be connected to a valve 510 that can open or close in response to pressure within the reservoir 506.

In the illustrated embodiment 500, a single reservoir driver 502 is illustrated. Alternatively, the device 500 can include a second reservoir driver connected to the second reservoir 506. The second reservoir driver can be configured to respond to conditions in the surrounding environment in a manner different from the first reservoir driver 502. For example, the second reservoir 506 can act to create a different response pressure than the first reservoir 502 in response to conditions of surrounding tissue. In a further embodiment, the device 500 can include more than two reservoirs and can include more than one reservoir driver.

In an exemplary embodiment, the reservoir driver 502 can be connected to the reservoirs 504 and 506. The reservoir driver 502 can be configured to motivate the reservoirs 504 and 506 to expel their respective agents in response to conditions of surrounding tissue, such as a nucleus pulposus. In an example, the reservoir driver 502 can include a hydraulic fluid to drive pistons associated with each reservoir 504 and 506. In another example, the reservoir driver 502 can include an expanding material, such as an osmotic material, that moves a piston associated with the reservoir 504 and a piston associated with the reservoir 506. For example, the reservoir driver 502 can be configured to apply pressure to a movable barrier between the reservoir driver 502 and at least one of the reservoirs (504 or 506), motivating agent from at least one of the reservoirs (504 or 506).

In a particular embodiment, the reservoir driver 502 can be an osmotic driver. For example, the reservoir driver 502 can include a membrane that is permeable to water or fluids of surrounding tissue. In a particular example, the membrane is sensitive to hydraulic pressure in surrounding tissue and permits fluid to permeate across the membrane in or out of the reservoir driver 502 in response to the hydraulic pressure. In another example, the osmotic driver includes an osmotic agent. For example, the osmotic agent can absorb water based on the hydraulic pressure of the surrounding tissue. An osmotic agent within the chamber can absorb water or fluid from the surrounding tissue and expand or increase pressure within the chamber. The osmotic agent can include a non-volatile water-soluble osmagent, an osmopolymer that swells on contact with water, or a mixture of the two. An osmotic agent, such as sodium chloride with appropriate lubricants, binders, or viscosity modifying agents, such as sodium carboxymethylcellulose or sodium polyacrylate can be prepared in various forms. Sodium chloride in tablet form is a water swellable agent. In various embodiments, the osmotic agent can generate between about 0 and about 36 MPa (about 5200 psi) of pressure.

Materials suitable for the fluid permeable membrane include those that are semipermeable and that can conform to the shape of the housing upon wetting and make a watertight seal with the rigid surface of the housing. The polymeric materials from which the membrane can be made vary based on the pumping rates and device configuration requirements and can include plasticized cellulosic materials, enhanced polymethylmethacrylate such as hydroxyethylmethacrylate (HEMA), elastomeric materials such as polyurethanes and polyamides, polyether-polyamide copolymers, thermoplastic copolyesters, or the like, or any combination thereof. In a particular example, the osmotic driver has a slow response, effectively responding to an average condition of the surrounding tissue.

In an exemplary embodiment, at least one of the valves (508 or 510) is configured to respond to pressure within at least one of the reservoirs (504 or 506). For example, the respective valve (508 or 510) can open or close based on the pressure within the respective reservoir (504 or 506). As a result, the respective valve (508 or 510) can open or close based on the condition of the tissue, which influences the reservoir driver 502 that in turn influences the respective reservoir (504 or 506).

Figure 6:
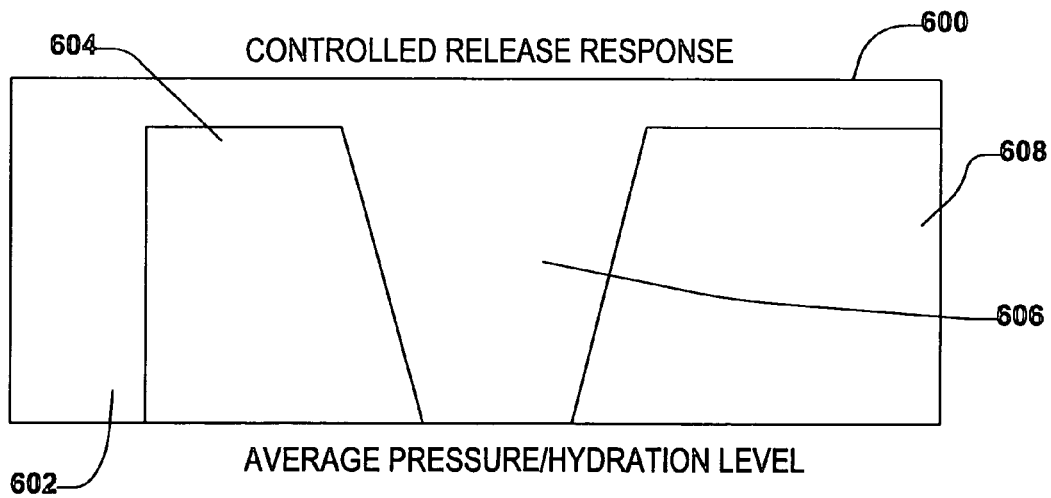
FIG. 6 includes a graphical illustration of a controlled release response.

In a particular example, at least one of the valves (508 or 510) can be configured to implement a controlled release response (i.e., configured to open or close to pressure within at least one of the reservoirs (504 or 506) based at least in part on the type of agent stored within the respective reservoir (504 or 506)). FIG. 6 includes an illustration of an exemplary controlled release response 600. For example, when the environment surrounding the device 500 has a very low average pressure or low hydration level, as illustrated at 602, no agent is released. Such a condition can exist prior to implanting the device. As such, the valves, 508 and 510, are closed.

When the average pressure or the hydration level of the surrounding environment is low (604), such as when the device has been implanted into an intervertebral disc having damage or having aged, the device can be configured to release a stimulating agent. For example, the device can be configured to release a regenerating agent.

When the average pressure or the hydration level of the surrounding tissue is acceptable, as illustrated at 606, the device can be configured to prevent the release of agents. For example, a valve associated with a reservoir storing a stimulating agent can be closed and a valve associated with a reservoir storing a degrading agent can be closed. Alternatively, a valve associated with a reservoir storing a therapeutic agent can be open.

When the average pressure or the hydration level of the surrounding tissue is high, as illustrated at 608, the device can be configured to release a degrading agent. For example, a valve associated with a reservoir storing degrading agent can be open and a valve associated with a reservoir storing a stimulating agent can be closed.

To affect such a control strategy, a valve connected to a reservoir including a stimulating agent can have two closed positions and a valve connected to a reservoir including a degrading agent can be configured to open at high pressures. For example, if the reservoir 504 includes a stimulating agent and the reservoir 506 includes a degrading agent, the valves 508 and 510 can be configured to implement the controlled release strategy illustrated in FIG. 6. When the reservoir drive is dehydrated, as can be the case as illustrated at 602, the valve 508 and the valve 510 can be closed. When the reservoir driver 502 is hydrated and the device is implanted in situ, the valves 508 and 510 can have an open or closed state based on the condition of the surrounding tissue. When the surrounding tissue is in a condition as illustrated at 604, the valve 508 can be open and the valve 510 can be closed. When the surrounding tissue is in a condition as illustrated at 606, the valves 508 and 510 can be closed, and when the tissue is in a condition as illustrated at 608, the valve 508 can be closed and the valve 510 can be open. In addition, the valves 508 and 510 can be configured to fail closed (i.e., when no pressure exists in the reservoirs (504 or 506), the valves 508 and 510 are closed).

In an exemplary embodiment, a refill port, such as the refill ports 512 and 514, can be coupled to the reservoir (504 or 506). The refill port (512 or 514) can be used to add an agent to the reservoir (504 or 506) prior to implanting the device, such as during manufacture or during configuration of the device for implanting. In addition, the refill port (512 or 514) can be used to add an agent to the reservoir (504 or 506) after use.

In a further exemplary embodiment, the device 500 can include a remote access component 516. The remote access component 516, for example, can couple to the reservoir driver 502. In an example, the remote access component 516 can respond to a magnetic field. In another example, the remote access component 516 can respond to an electromagnetic signal, such as a radio frequency signal. In a further example, the remote access component 516 can respond to a light signal, such as an infrared signal. In an additional example, the remote access component 516 can respond to a wave signal, such as an ultrasonic signal. In response to a signal from a location external to a patient, the remote access component 516 sends an electrical signal to the reservoir driver 502. In another example, the remote access component 516 can respond to a first oscillating frequency with a first response and can respond to a second oscillating frequency with a second response. The first response can be communicated to a first reservoir driver and the second response can be communicated to a second reservoir driver.

In a particular example, the remote access component 516 can include at least one induction coil. When an oscillating field induces current within the coil, the reservoir driver 502 can adjust, influencing the pressure within one or more reservoirs (504 or 506). In a further example, the device 500 can include more than one reservoir driver 502. For example, the device 500 can include an osmotic reservoir driver and an electro-mechanical reservoir driver activated by the remote access component 516. In a particular example, a single reservoir can be connected to an osmotic driver and an electro-mechanical driver.

The device, such as device 500 illustrated in FIG. 5, can be included in a housing. The housing can form a cylinder, sphere, capsule, disc, cone, coil shape, or any combination thereof. In an example, the housing can surround each of the components of the device. Alternatively, the individual components can be included within one or more housings.

The housing can have a smallest dimension not greater than about 8 mm. For example, the smallest dimension can be not greater than about 5 mm, such as not greater than about 3 mm. In a particular example, a cylindrical housing can have a diameter that is not greater than about 8 mm. In an exemplary capsule-shaped housing, the diameter around the center is not greater than about 8 mm.

The housing can be formed of a metallic material, a polymeric material, or any combination thereof. An exemplary polymeric material can include polypropylene, polyethylene, halogenated polyolefin, fluoropolyolefin, polybutadiene, polysulfone, polyaryletherketone, polyuerethane, polyester or copolymers thereof, silicone, polyimide, polyamide, polyetherimide, a hydrogel, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

Figure 7:
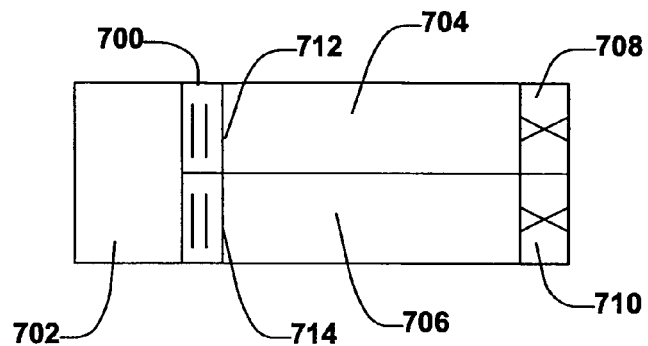
FIG. 7, FIG. 8, FIG. 9, FIG. 10, FIG. 11, and FIG. 12 include illustrations of exemplary controlled release devices.
Figure 8:
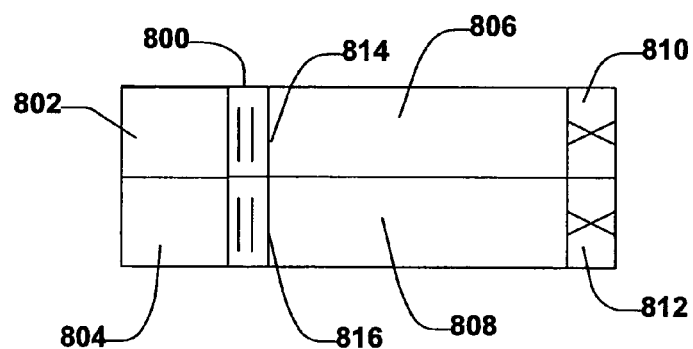

FIG. 7, FIG. 8, FIG. 9, FIG. 10, FIG. 11 and FIG. 12 include illustrations of exemplary embodiments of a controlled release device. For example, FIG. 7 and FIG. 8 illustrate a side-by-side configuration of a two-reservoir device. FIG. 7 illustrates an exemplary device 700 including a single reservoir driver 702 connected by movable barriers 712 and 714 to reservoirs 704 and 706, respectively. The reservoir driver 702 can impart pressure through the barrier 712 and 714 to influence the pressure of the reservoirs 704 and 706 respectively. In response to the pressure of the reservoirs 704 and 706, the valves 708 and 710, respectively, can open or close. FIG. 8 illustrates an exemplary device 800 including two reservoir drivers 802 and 804. The reservoir driver 802 can act through movable barrier 814 to influence the pressure of reservoir 806, which in turn influences the position of valve 810. The reservoir driver 804 can act through movable barrier 816 to influence the pressure of reservoir 808, which in turn influences the position of valve 812.

Figure 9:
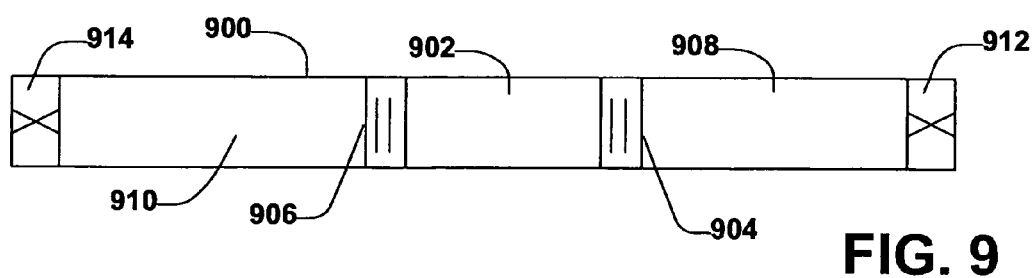
Figure 10:
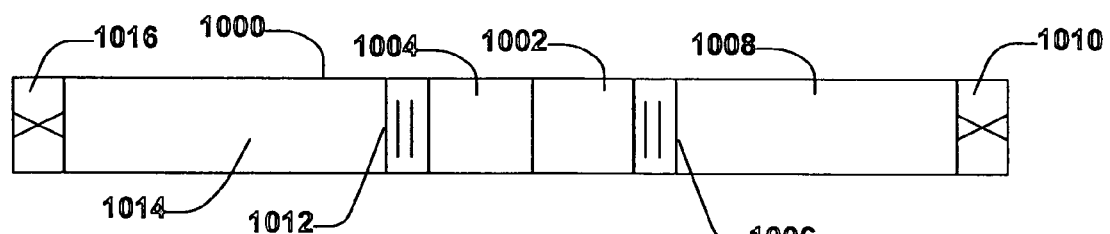

FIG. 9 and FIG. 10 include illustrations of another configuration of a two-reservoir device. For example, FIG. 9 illustrates a device 900 in which a single reservoir driver 902 can expand in opposite directions to influence the pressure in reservoirs 908 and 910. For example, the reservoir driver 902 can expand in a first direction, moving the barrier 904 to influence the pressure in reservoir 908, which in turn influences the position of the valve 912. In addition, the reservoir driver 902 can act in a second direction opposite the first direction, moving the barrier 906 to influence the pressure in the reservoir 910, which in turn influences the position of the valve 914. FIG. 10 includes an illustration of a two-reservoir driver embodiment 1000. For example, the reservoir driver 1002 can act in a first direction to move the barrier 1006 to influence the pressure in the reservoir 1008 and the position of the valve 1010. In addition, the reservoir driver 1004 can act in a second direction opposite the first direction to move the barrier 1012 to influence the pressure in the reservoir 1014 and the position of the valve 1016.

Figure 11:
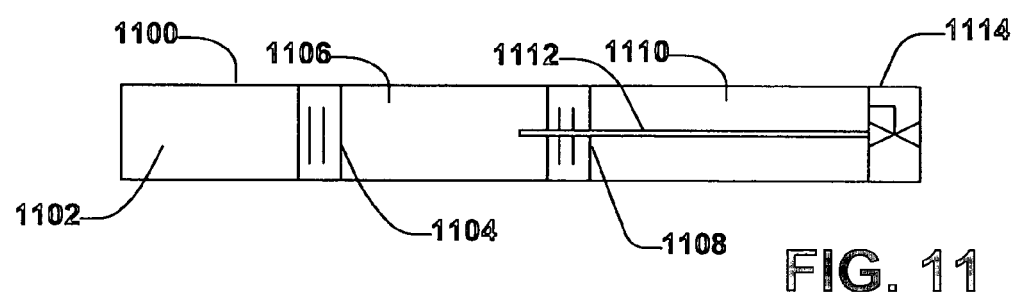

In a further exemplary embodiment, FIG. 11 illustrates a device 1100 including aligned reservoirs. For example, a reservoir driver 1102 can act on a movable barrier 1104 to influence the pressure in reservoir 1106. The pressure in reservoir 1106 can act on the movable barrier 1108 to influence the pressure of the reservoir 1110. A fluid channel 1112 can connect the reservoir 1106 to the valve assembly 1114. In an exemplary embodiment, the valve assembly 1114 includes a three-way valve. In another example, the valve assembly 1114 includes two valves. The exemplary devices (900, 1000, and 1100) of FIG. 9, FIG. 10, and FIG. 11, can be housed in a cylindrical housing.

Figure 12:
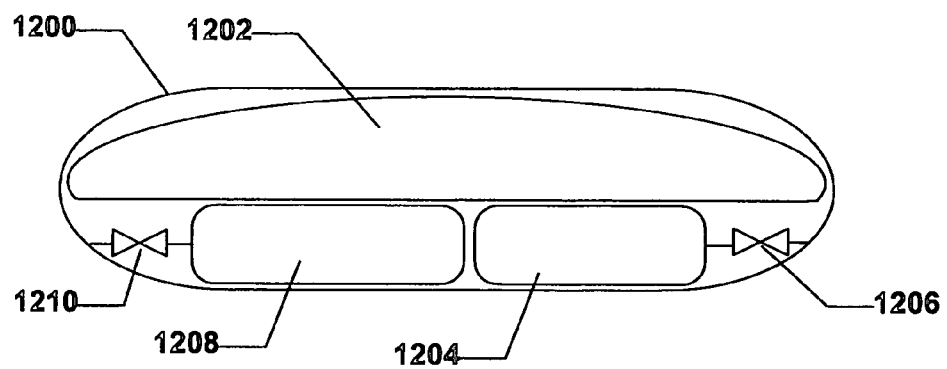

In another exemplary embodiment, a capsule shaped housing or a disc-shaped housing can be used. FIG. 12 illustrates a device 1200 that includes a reservoir driver 1202 overlying a reservoir 1208 and a reservoir 1204. The valves 1206 and 1210 can be connected to the reservoirs 1204 and 1208, respectively. In the exemplary embodiment illustrated in FIG. 12, a larger surface area of the device 1200 can be used for fluid transfer into and out of the reservoir driver 1202 than in other configurations described above.

Figure 17:
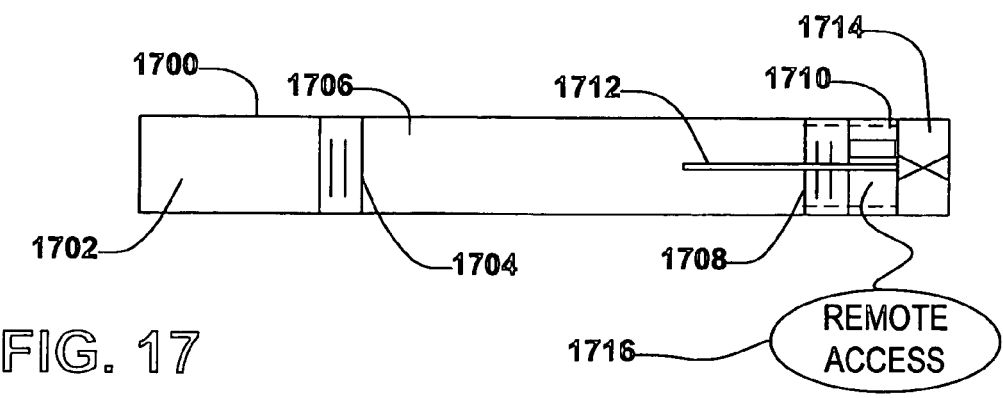
FIG. 17 includes an illustration of an exemplary controlled release device.

In a further exemplary embodiment, FIG. 17 illustrates a device 1700 including a second reservoir driver 1710 attached to a reservoir 1706. For example, a reservoir driver 1702 can act on a movable barrier 1704 to influence the pressure in the reservoir 1706 as described above in relation to other embodiments. The second reservoir driver 1710 can act on the reservoir 1706 via barrier 1708. For example, the second reservoir driver 1710 can act to increase the pressure of the reservoir 1706 in response to a signal from a remote access component 1716. A fluid channel 1712 can connect the reservoir 1706 to the valve assembly 1714, which responds to the pressure in the reservoir 1706. In an alternative embodiment, the device 1700 can include one or more additional reservoirs and one or more additional drivers. For example, an implanted device 1700 can act to release agent in response to a signal from a device external to the patient. In an example, a healthcare provider can perform a scan, such as a CT scan or an MRI scan, to determine a condition of an intervertebral disc. Based on the results of the scan, the healthcare provider can activate the device via the remote access component to adjust the release of agents.

Figure 13A:
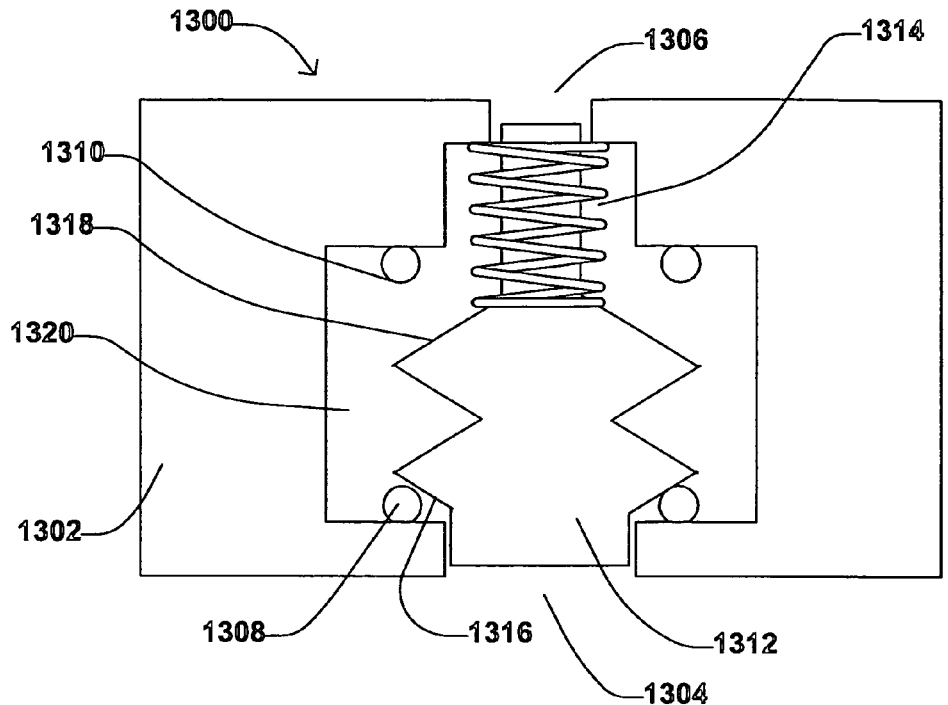
FIG. 13a, FIG. 13b, FIG. 13c, FIG. 14a, and FIG. 14b include illustrations of exemplary valves.
Figure 13B:
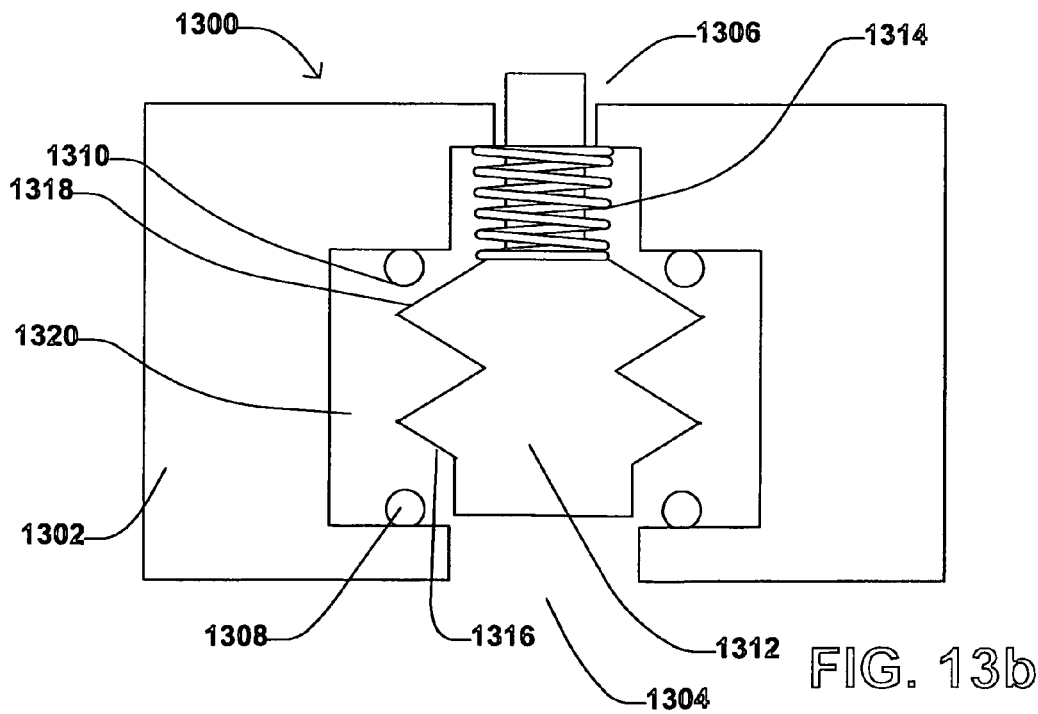
Figure 13C:
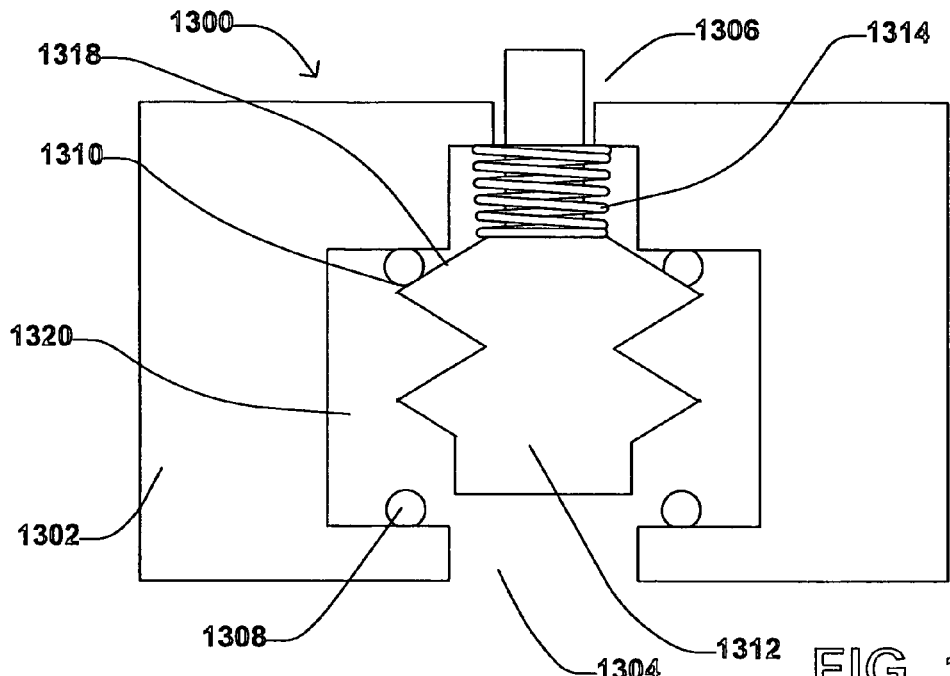

To implement a control strategy, the valves coupled to the reservoirs can be configured to behave in a manner that correlates with the control strategy. For example, a valve coupled to a reservoir including a stimulating agent can be configured to open in response to a specific range of low average pressure or low tissue hydration and close at other times. In a particular example, a valve coupled to a reservoir storing a stimulating agent can be configured to have two closed positions. FIG. 13a, FIG. 13b, and FIG. 13c illustrate an exemplary valve 1300, which can have a valve body 1302, a stem 1312, and a spring 1314. The valve body 1302 can include an opening 1304 in communication with a reservoir and an opening 1306 configured to be an effluent opening. The valve body 1302 also can include a chamber 1320 in communication with the openings 1304 and 1306, forming a fluid path therethrough. In addition, the valve 1300 can include a first valve seat 1308 proximate to the valve opening 1304 and a second valve seat 1310 opposite the first valve seat 1308.

In an exemplary embodiment, the valve body 1302 can be formed of metallic material, a polymeric material, or any combination thereof. An exemplary polymeric material can include polypropylene, polyethylene, halogenated polyolefin, fluoropolyolefin, polybutadiene, polysulfone, polyaryletherketone, polyuerethane, polyester, or copolymers thereof, silicone, polyimide, polyamide, polyetherimide, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

The valve stem 1312 can form a first seal 1316 configured to engage the first valve seat 1308 and a second seal 1318 configured to engage the second valve seat 1310. The valve stem 1312 can be formed as a single integrated part or can be formed of multiple attached parts. In an example, the valve stem can be formed of metallic material, a polymeric material, or any combination thereof. An exemplary polymeric material can include polypropylene, polyethylene, halogenated polyolefin, fluoropolyolefin, polybutadiene, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

In an exemplary embodiment, the spring 1314 can surround a portion of and engage the valve stem 1312 to provide a motivating force in a direction away from the effluent opening 1306 and toward the inlet opening 1304. In an example, the spring 1314 can be a helical compression spring and can be formed of a resilient metal or polymer.

As illustrated at FIG. 13a, the valve spring 1314 can press the valve stem 1312 toward the inlet opening 1304. When the pressure in the reservoir is low, the seal 1316 of the valve stem 1312 can press against the valve seat 1308. As the pressure within the reservoir increases, the force against the valve stem 1312 can increase to counteract the force of the spring 1314. As illustrated at FIG. 13b, a sufficient pressure within the reservoir results in an unseating of the seal 1316 from the valve seat 1308, resulting in a passage through the opening 1304, the chamber 1320, and the opening 1306. As the pressure further increases, the seal 1318 of the valve stem 1312 can press against the valve seat 1310, closing the passage and preventing further agent flow. In a particular embodiment, such a valve can remain closed when the device is not in service, can open in response to a low average pressure or low hydration condition in a surrounding tissue, and can be closed based on other conditions in a surrounding tissue. In another exemplary embodiment, the valve can be used in conjunction with a therapeutic agent and can open during intermediate conditions of surrounding tissue, while closing during other conditions.

Figure 14A:
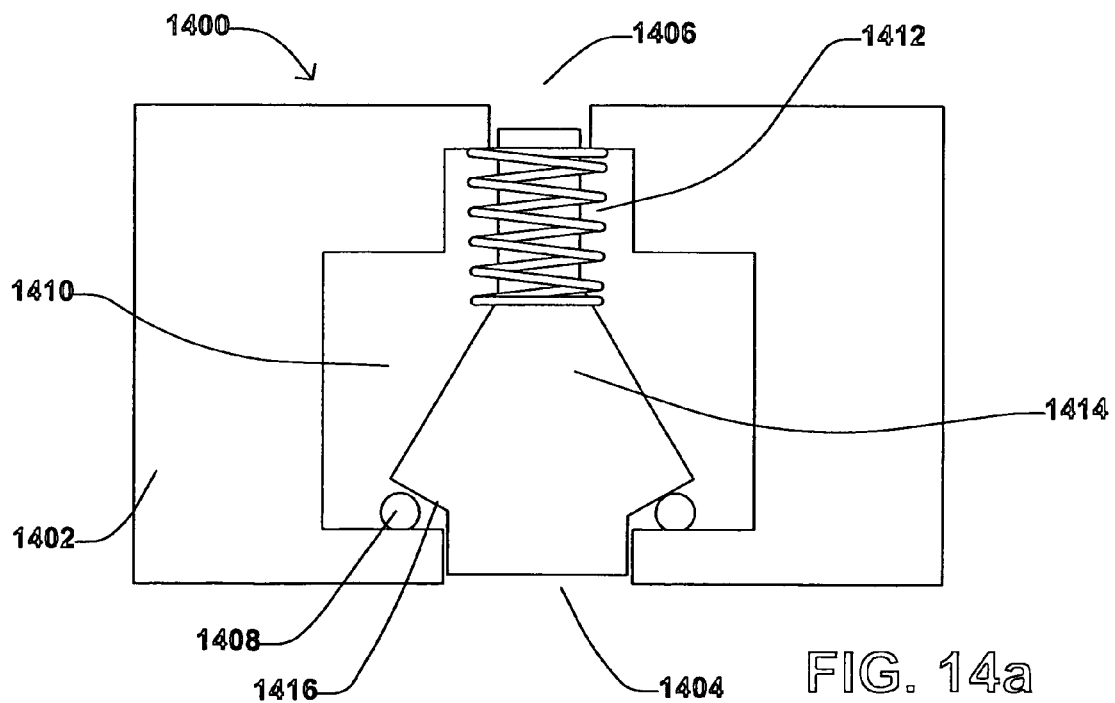
Figure 14B:
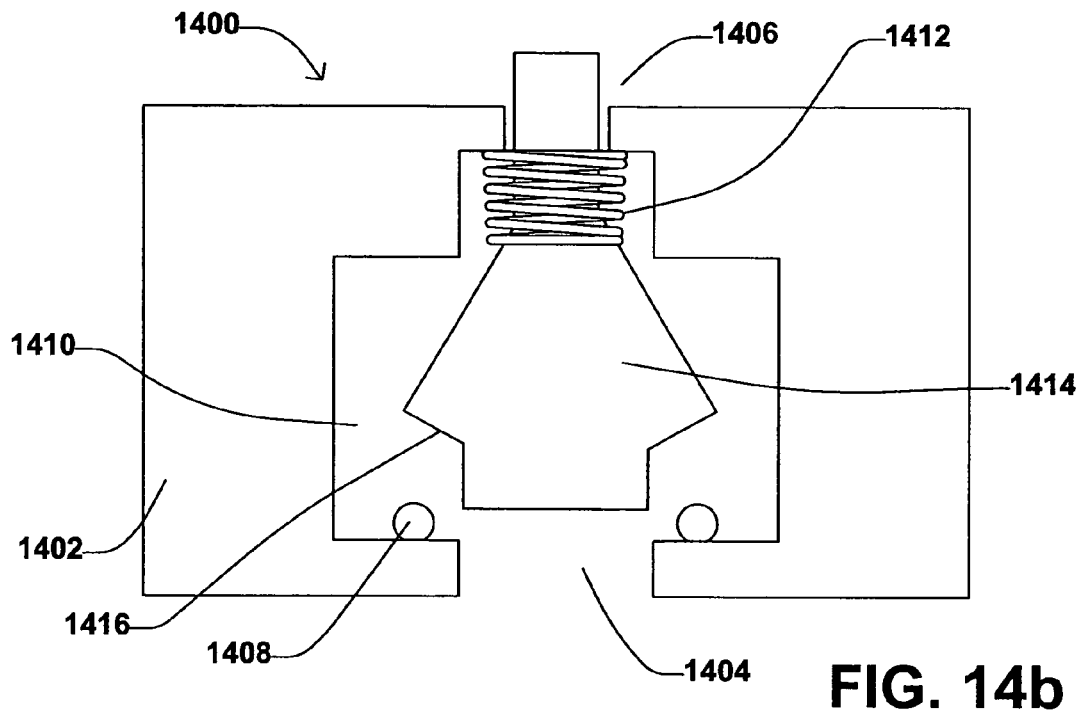

In another exemplary embodiment, FIG. 14a and FIG. 14b include illustrations of an exemplary valve 1400. The valve 1400 can include a valve body 1402 having an inlet opening 1404, a chamber 1410, and an effluent opening 1406. The valve body also can include a valve stem 1414 and a spring 1412. The spring 1412 can surround a portion of and can engage the valve stem 1414 to provide a motivating force away from the effluent opening 1406 and toward the inlet opening 1404.

The valve body 1402 can include a seat 1408 and the valve stem 1414 can include a seal 1416 configured to engage the seat 1408. As illustrated at FIG. 14a, the seal 1416 can engage the seat 1408 to prevent agent flow from a reservoir. In particular, the valve 1400 can be in the closed position illustrated in FIG. 14a when the reservoir has a pressure that is insufficient to overcome the force of the spring 1412. When the pressure increases, the valve 1400 can move to an open position illustrated in FIG. 14b in which the seal 1416 disengages from the seat 1408. Such a valve 1400 can be used in conjunction with a reservoir storing degrading agent, for example.

While the valves illustrated in FIG. 13a, FIG. 13b, FIG. 13c, FIG. 14a, and FIG. 14b are described in relation to specific control strategies for agent release, such valves can be used to implement other control strategies. Further, the valves can be configured based on their selection and the selection of components, such as springs. For example, a spring can be selected such that the valve opens or closes in response to a selected pressure or range of pressures selected from ranges between about 0.1 to about 2000 psi, such as between about 0.5 to about 100 psi. In addition, such valves are provided as examples, and other valves not illustrated can be used to implement the described control strategy.

Exemplary Method of Use

Figure 15:
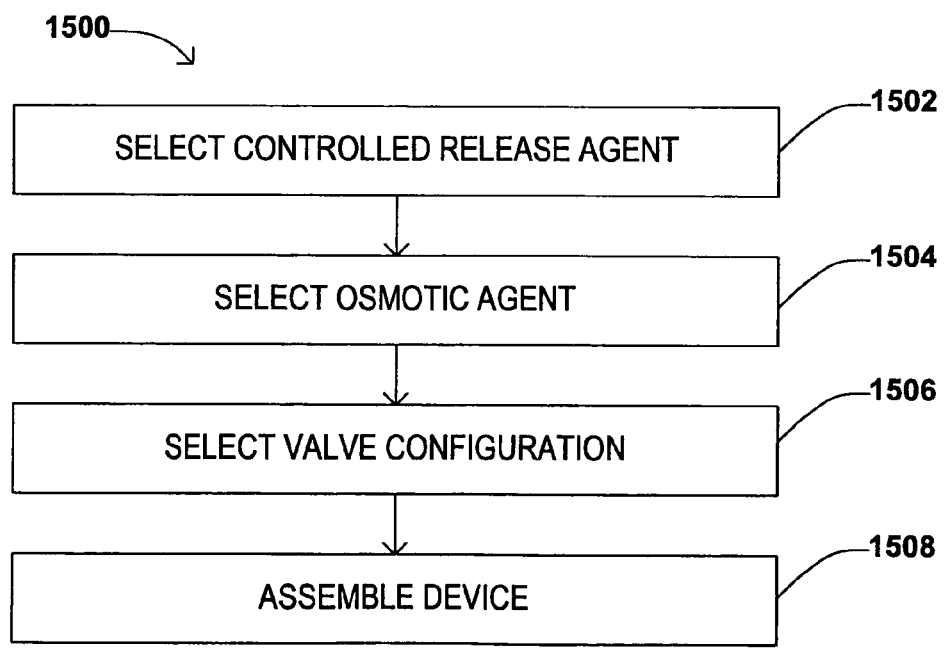
FIG. 15 includes a flow diagram of an exemplary method for preparing a controlled release device.

In an exemplary method, the device can be configured to implement a desired controlled release strategy. FIG. 15 includes an illustration of an exemplary method 1500 to configure a device for a particular patient condition. For example, an agent can be selected for each reservoir of the device, as illustrated at 1502. A device including a single reservoir can include a degrading agent, for example. In another example, a device including two or more reservoirs can include two or more agents. In a particular example, a device including two or more reservoirs can include a stimulating agent, such as a regenerating agent, in at least one of the reservoirs.

Based on the agents selected, a controlled release strategy can be implemented by configuration of the reservoir driver and valves. For example, an osmotic agent can be selected, as illustrated at 1504. In a particular example, the osmotic agent and concentrations and variations thereof can be selected to provide a particular response to average pressure or hydration conditions of surrounding tissue. In particular, the osmotic agent can provide a desired pressure response to conditions of the tissue, such as the nucleus pulposus.

In conjunction with the expected pressure response of the osmotic agent, a valve configuration can be selected, as illustrated at 1506. For example, springs can be selected that provide the prescribed response to the expected pressures effected by the osmotic agent, in situ.

Once a configuration is selected, the device can be configured and assembled, as illustrated at 1508. For example, the device can be configured at the time of manufacture based on an expected application. In another example, the device can be configured by a healthcare provider prior to implantation. In a particular example, the selected agents can be injected into the reservoirs by refill ports, the springs can be added to the valve assemblies, and a cartridge including the osmotic agent can be placed within the device.

Device Implantation

Figure 16:
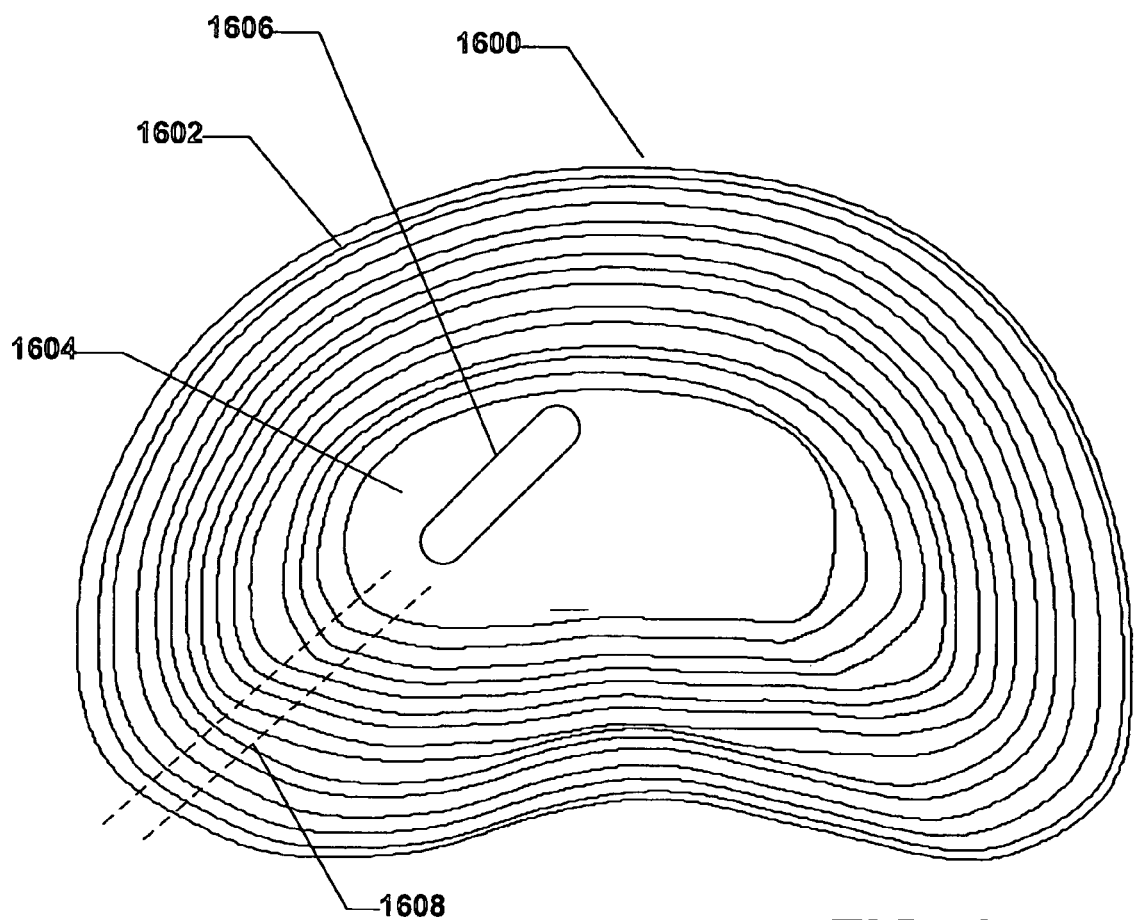
FIG. 16 includes an illustration of an exemplary intervertebral disc.

The device or at least a portion of the device can be inserted into the nucleus pulposus of an intervertebral disc of a patient. For example, the device can be implanted as a whole within the nucleus pulposus. FIG. 16 includes an illustration of an exemplary intervertebral disc 1600 including an annulus fibrosis 1602 and a nucleus pulposus 1604. A device 1606 can be inserted into the nucleus pulposus 1604 through a passage 1608 through the annulus fibrosis 1602. In an example, the passage 1608 is formed using an instrument having a lumen through which the device 1606 can be guided. Once the device 1606 is inserted into the nucleus pulposus 1604, the passage 1608 in the annulus fibrosis 1602 can be sealed using a tissue sealant, scaffold plug, or any combination thereof. In a particular example, the tissue sealant or scaffold plug includes regenerative agents, such as growth factors.

Patient Treatment using an Implantable Device

Typically, the embodiments of the implantable controlled release device described above can be used to treat conditions associated with an intervertebral disc. For example, a patient can have undergone a prior discectomy or can have experienced a herniated disc. In another example, a scan of the patient, such as a computed tomography (CT) scan or a magnetic resonance imaging (MRI) scan, can indicate a problem in a particular intervertebral disc. In such a case, a device can be implanted in the patient.

In general, the device can be configured and filled with an agent or agents prior to implantation. The device can be implanted within the nucleus pulposus of the intervertebral disc and release agent or agents in response to conditions within the intervertebral disc. For example, once implanted, an osmotic driver can hydrate, resulting in a pressure within a reservoir. Based on the pressure within the reservoir, a valve can open or close and release or prevent the release of an agent.

The device can be included in a kit that includes agents to be inserted into the device. The kit can also include one or more osmotic agents and can include one or more valve springs or valves. Alternatively, the device can be provided with the agent within the device. In addition, the device can include a refill port. An agent can be injected into the port to refill a reservoir.

CONCLUSION

With the implanted device described above, the condition of an intervertebral disc can be maintained within a range of acceptable states. As such, the chance of herniation, exacerbation of previous herniated injuries, and degradation of the disc can be reduced. Such a device can further reduce the likelihood that a more invasive disc replacement implant is used. In a particular embodiment, a healthcare provider can manipulate the performance of the device to provide long term treatment to the intervertebral disc, reducing patient discomfort, patient pain or neuro-deficit, and disc degeneration and delaying additional spinal surgery.

The above-disclosed subject matter is to be considered illustrative, and not restrictive, and the appended claims are intended to cover all such modifications, enhancements, and other embodiments that fall within the true scope of the present invention. For example, it is noted that the components in the exemplary embodiments described herein as having a particular function or as being located in a particular housing are illustrative and it is noted that such components can perform additional functions or be located in different configurations. Thus, to the maximum extent allowed by law, the scope of the present invention is to be determined by the broadest permissible interpretation of the following claims and their equivalents, and shall not be restricted or limited by the foregoing detailed description.

What is claimed is:

1. A device comprising:
  a first reservoir;
  a second reservoir;
  a first valve in fluid communication with the first reservoir, the first valve configured to open based on a first tissue condition of pressure or hydration;
  a second valve in fluid communication with the second reservoir, the second valve configured to open based on a second tissue condition and wherein the second valve is configured to close based on the first tissue condition; and
  a first osmotic driver coupled to the first reservoir, wherein the first osmotic driver is configured to adjust a pressure of the first reservoir based on a condition of a tissue of pressure or hydration.

2. The device of claim 1, wherein the first valve is configured to close based on the second tissue condition.

3. The device of claim 1, wherein the first reservoir is configured to include a first agent, wherein the first agent is a first stimulating agent.

4. The device of claim 3, wherein the second reservoir is configured to include a second agent, and wherein the second agent is a second stimulating agent.

5. The device of claim 4, wherein the first stimulating agent is a regenerating agent.

6. The device of claim 4, wherein the second stimulating agent is a therapeutic agent.

7. The device of claim 3, wherein the second reservoir is configured to include a second agent, and wherein the second agent is a degrading agent.

8. The device of claim 7, wherein the degrading agent is selected from the group consisting of chymopapain, collagenase, chondroitinase, keratanase, human proteolytic enzymes, papaya protenase, or any combination thereof.

9. The device of claim 1, wherein the first tissue condition is associated with a low average pressure in a tissue.

10. The device of claim 1, wherein the second tissue condition is associated with a high average pressure in a tissue.

11. The device of claim 1, wherein the first osmotic driver is coupled to the second reservoir.

12. The device of claim 1, further comprising a second osmotic driver coupled to the second reservoir.

13. The device of claim 12, wherein the first and second osmotic drivers have a different response to a condition of a tissue.

* * * * *